United States Patent [19]

Privitera et al.

[11] Patent Number: 5,569,291

[45] Date of Patent: Oct. 29, 1996

[54] SURGICAL PENETRATION AND DISSECTION INSTRUMENT

[75] Inventors: Salvatore Privitera, West Chester; Richard F. Schwemberger, Cincinnati, both of Ohio

[73] Assignee: Ethicon Endo-Surgery, Inc., Cincinnati, Ohio

[21] Appl. No.: 382,461

[22] Filed: Feb. 1, 1995

[51] Int. Cl.$^6$ .................................................. A61M 5/18
[52] U.S. Cl. .................................... 606/185; 604/164
[58] Field of Search .................................. 606/184, 185; 604/164–166, 264, 274, 174; 128/3, 4, 6

[56] References Cited

U.S. PATENT DOCUMENTS

| | | |
|---|---|---|
| 4,535,773 | 8/1985 | Yoon . |
| 5,226,426 | 7/1993 | Yoon . |
| 5,271,380 | 12/1993 | Riek et al. . |
| 5,290,243 | 3/1994 | Chodorow et al. ............. 606/185 |
| 5,290,294 | 3/1994 | Cox et al. ............. 604/164 |
| 5,312,351 | 5/1994 | Gerrone ............. 604/264 |
| 5,334,150 | 8/1994 | Kaali . |
| 5,356,421 | 10/1994 | Castro ............. 606/185 |
| 5,441,041 | 8/1995 | Sauer et al. ............. 606/185 |

OTHER PUBLICATIONS

United States Surgical Corporation, VISIPORT* Disposable Optical Trocar Insert, Norwalk, Connecticut, 1994.

Primary Examiner—Gary Jackson
Assistant Examiner—William Lewis
Attorney, Agent, or Firm—Matthew S. Goodwin

[57] ABSTRACT

A surgical instrument for penetrating or dissecting bodily tissue which provides for the capability for simultaneous visualization during penetration or dissection is disclosed. An endoscope can be inserted through the hollow shaft of the instrument to visualize the penetration or dissection. A locking assembly is featured which enables the user to initially slide the endoscope through the hollow shaft for proper positioning before the instrument is advanced into tissue, and then lock the endoscope in place to prevent substantial movement of the endoscope during advancement into tissue.

7 Claims, 6 Drawing Sheets

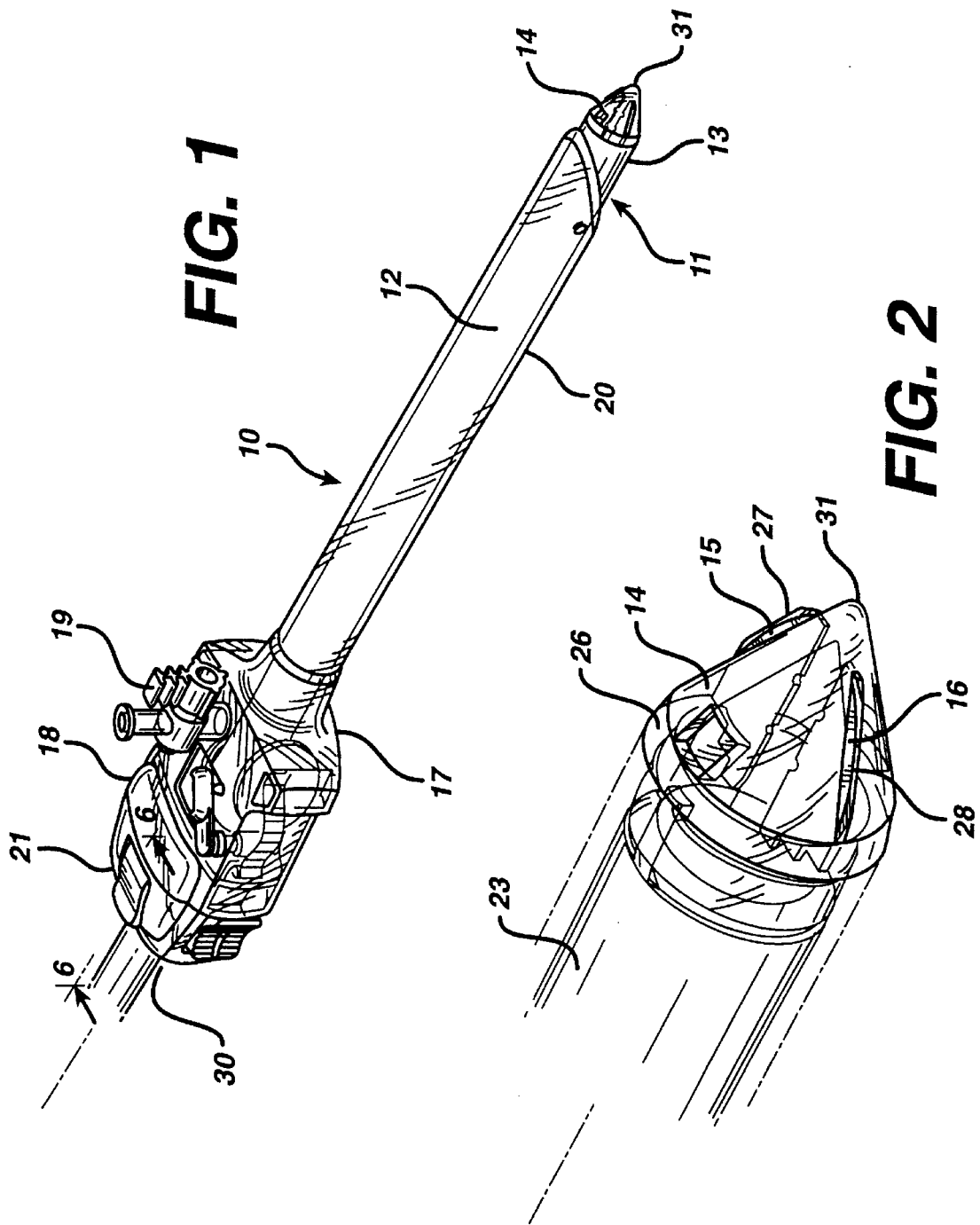

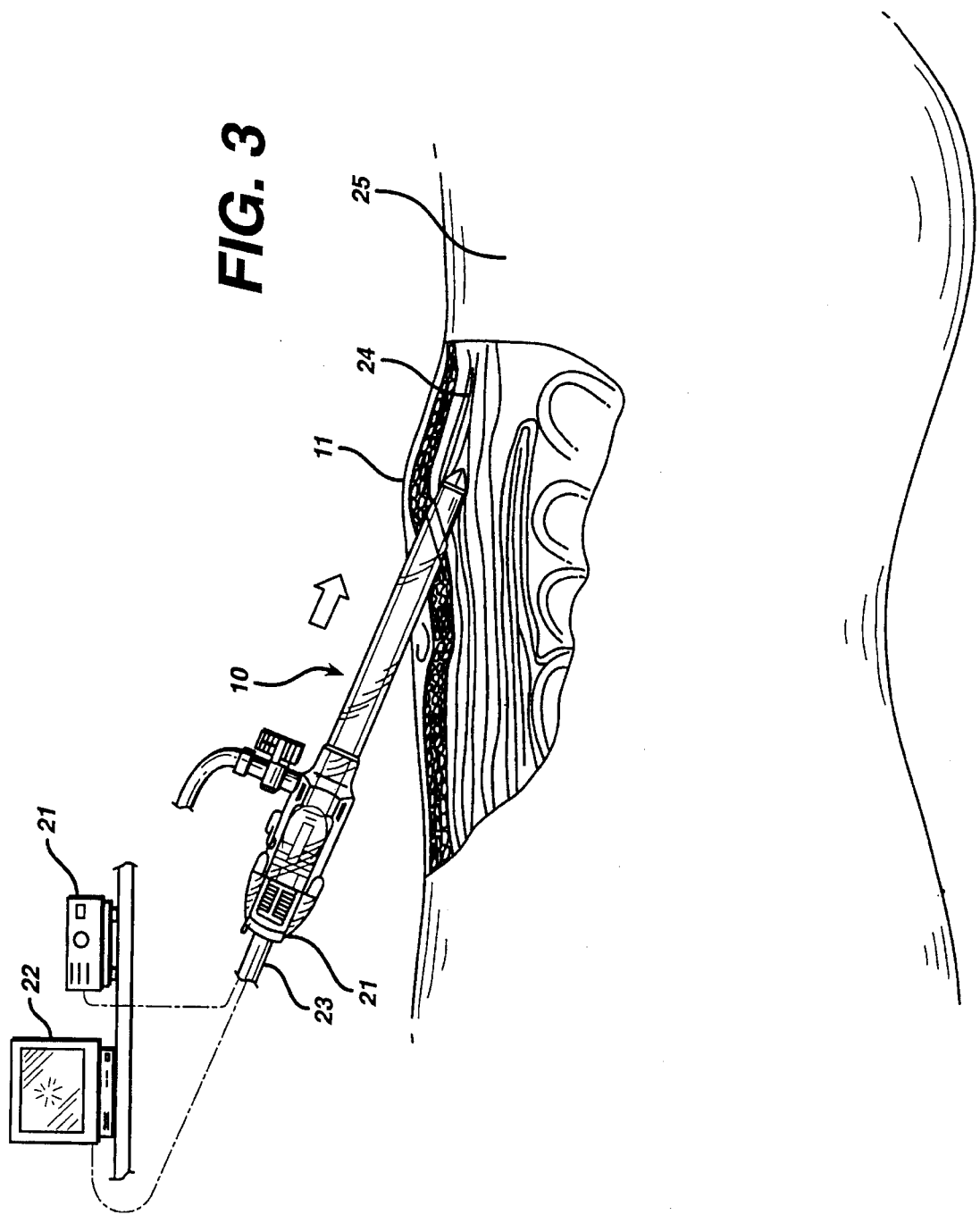

SURGICAL PENETRATION AND DISSECTION INSTRUMENT

BACKGROUND OF THE INVENTION

This invention relates to surgical instruments for penetrating or dissecting bodily tissue. More specifically, it relates to penetrating instruments which desirably but not necessarily incorporate an imaging element for viewing. These instruments allow access into a body cavity, or facilitate the creation of space between tissue layers, when the instrument is advanced into the tissue, and simultaneously provide the ability to visualize the penetrated or dissected tissue during the advancement.

Key surgical activities which are required during numerous surgical procedures are the creation of: a) an access opening into the body cavity at the desired surgical site, and b) space between adjacent tissue layers to provide room for manipulating instruments and performing the surgical procedure. For many years, the surgeon created the access opening by simply making a large incision through the body wall to expose the body cavity. Similarly, space between adjacent tissue layers was created by making the large incision and then dissecting away the unwanted tissue layers. The length of the incision would depend on the size of conventional surgical instruments and the ability of the surgeon to properly and efficiently use these instruments within the body cavity through the incision created. Once the surgeon finished the surgical procedure, the incision could be fastened using known techniques. Unfortunately, due to the nature of these conventional, open surgical procedures, long incisions were often necessary. Open surgery can therefore be traumatic to the patient because, among other things, the recuperative period required to fully heal from the effects of the large incision may be significant.

Since a patient's recuperative period can be significant in connection with conventional open surgery, new surgical procedures and instruments to support those procedures are becoming available. The most popular alternative to open surgery currently is endoscopic surgery. Endoscopic surgery involves the use of a number of small diameter openings providing access into the body cavity. Unlike the large incisions required for open surgery, these small diameter openings readily heal following surgery, and require much less recuperation time for the patient.

The cornerstones which have made endoscopic surgical procedures possible are the miniaturized camera, or endoscope, and the surgical penetration instrument providing the small diameter opening for access into the body cavity, conventionally referred to as the trocar. Since both of these instruments are critical for the performance of endoscopic surgery, each will be discussed briefly below.

An endoscope is an elongated, generally cylindrical imaging and visualization instrument. It can be attached to a light source which provides illumination within the body cavity at the surgical site. The endoscope contains a miniaturized camera lens which is capable of transmitting the illuminated images at the surgical site to the surgeon during a surgical procedure. The endoscope is frequently attached to a video monitor during endoscopic surgery, so that the surgical team can observe the surgical procedure within the body cavity on the video monitor screen. The endoscope has made it possible to indirectly observe the surgical procedure without having the direct access into the body cavity, and consequently the large incisions it requires to create such direct access.

Critical to the success of endoscopic surgery is the creation of a small diameter passageway into the body cavity for subsequent insertion and withdrawal of surgical instruments. These instruments include, for example, an endoscope, and elongated instruments to cut, fasten, coagulate and excise desired tissue. The trocar has become the instrument of choice to create this small diameter passageway. A trocar is a penetrating assembly including a cutting tool, commonly referred to as the trocar obturator. The obturator has an elongated, cylindrical shaft from which extends a penetrating tip to create and enlarge an opening into tissue as the obturator is advanced. The obturator is slidably received in a sleeve, commonly referred to as the trocar cannula. As the obturator is advanced into the tissue, the cannula likewise is advanced. When the obturator has completely punctured the body wall, the obturator is withdrawn from the trocar assembly, leaving behind the trocar cannula. The trocar cannula then provides the passageway into the body cavity through a relatively small diameter opening.

One of the first technical challenges in connection with the design and manufacture of the trocar related to the incorporation of features into the trocar to enhance its safety. Specifically, it was important to develop a safety trocar which could substantially lessen the possibility of unintentional tissue or organ puncture. The seminal patent that describes a mechanism for protecting bodily tissue and organs from inadvertent puncture during advancement of the instrument into the body cavity is U.S. Pat. No. 4,535,773 (Yoon, issued August, 1985). This patent describes a trocar assembly which includes a safety shield interposed between the trocar obturator and cannula. The shield is biased in an extended position to cover the penetrating tip of the obturator. When the surgeon desires to penetrate tissue with the trocar, the safety shield retracts and exposes the penetrating tip when the surgeon applies pressure against the body wall. The shield remains in the retracted position so long as pressure is continuously applied. When the surgeon fully punctures the body wall, the pressure is relieved and the safety shield returns to its extended position covering the penetrating tip. Therefore, inadvertent puncture of bodily tissue and organs within the body cavity can be avoided. Another trocar assembly with a safety shield mechanism is described in U.S. Pat. No. 5,226,426 (Yoon, issued Jul. 13, 1993). This patent describes a trocar obturator in the form of a hollow needle through which the safety shield (or safety "probe"), is disposed. Once again, the safety probe covers the sharp tip of the needle until pressure is applied during insertion.

Since the development of the safety-shielded trocar, other mechanisms for protecting tissues and organs from inadvertent puncture during endoscopic surgery have been developed. For example, mechanisms have been developed where the obturator retracts into the trocar cannula after puncture. These "retractable obturator" trocars may be equipped with a safety shield which simultaneously moves to an extended position as the obturator retracts within the trocar cannula.

While numerous trocar assemblies have been designed to prevent inadvertent puncture, all of these instruments still have one basic problem. Regardless of the safety mechanisms built into these instruments, the surgeon cannot avoid the fact that he is still puncturing tissue blindly. Not only is the puncture performed blindly, but the instruments are expensive to manufacture and occasionally fail in connection with the safety features incorporated to prevent inadvertent puncture during the blind insertion. Therefore, significant new designs for trocar assemblies have been developed.

One of the more remarkable developments in the design of trocar assemblies relates to the incorporation of visualization concurrently with penetration. This has been made possible by the "marriage" of the endoscope for imaging and visualization, and the trocar for penetration to provide the endoscopic access opening. The first patent to describe a surgical penetration instrument adapted for visualization during penetration is U.S. Pat. No. 5,271,380 (Riek, et al., issued Dec. 21, 1993). The Riek patent describes a penetrating instrument including a hollow, cylindrical sleeve and an imaging element attached to the sleeve at its distal end. The imaging element is a transparent, optical "window". In a preferred embodiment, it has a conical configuration to facilitate the advance of the instrument into body tissue. A fiber optic cable extends through the hollow shaft and is positioned adjacent the proximal end of the window. It delivers light from a light source through the optical window into surrounding bodily tissue. A camera lens is also provided in the shaft to deliver illuminated images transmitted through the optical window to the surgeon. When the surgeon advances the instrument into bodily tissue, the surgeon can view the tissue in front of and surrounding the optical window during the penetration. This feature is significant because the surgeon can adjust the path of advancement if he approaches tissue or organs which should not be touched. In this way, the incorporation of a safety shield or another mechanism to protect tissue or organs from inadvertent puncture during a blind insertion is unnecessary.

Another recently issued patent representing yet another significant advance in the state of the art with respect to surgical penetration instruments providing simultaneous visualization is U.S. Pat. No. 5,334,150 (Kaali, issued Aug. 2, 1994). The Kaali patent also describes an instrument including an elongated hollow shaft to which is attached an imaging element in the preferred form of a transparent conical window. However, instead of extending a fiber optic cable and lens into fixed positions adjacent the proximal end of the transparent window within the hollow shaft, the Kaali patent describes using a fully integrated endoscope which can be inserted through the hollow shaft adjacent the window to provide illumination and visualization of tissue in front of and surrounding the transparent window during insertion.

The surgeon using the penetrating instruments described in the Riek and Kaali patents must advance the instrument while the endoscope is positioned adjacent the transparent optical window within the shaft. Unfortunately, as the instrument is advanced, there is a strong likelihood that substantial movement of the endoscope within the shaft may occur. This movement will disrupt the visual image of the surrounding tissue, causing an unwanted distraction.

While significant advances have been made in the development of surgical penetrating instruments adapted for simultaneous visualization using an endoscope, there are still certain problems which need to be overcome. Significantly, it would be most desirable if a mechanism were developed to prevent the endoscope when fully inserted through the hollow shaft of the surgical penetration instrument from any substantial movement.

SUMMARY OF THE INVENTION

The invention is a surgical instrument for penetrating or dissecting bodily tissue. It comprises a generally cylindrical, elongated hollow shaft having a longitudinal axis and proximal and distal ends. The hollow shaft has a lumen through it with a diameter sized to slidably receive an endoscope therein from the proximal to the distal end of the shaft. A hub is attached to the proximal end of the shaft and has a passageway through it communicating with the shaft lumen. An endoscope locking assembly is on the hub. When the endoscope is received in the shaft lumen, the lock is actuable from an open position where the lock is spaced from the shaft lumen and disengaged from the endoscope, to a closed position where the lock constricts the shaft lumen and engages the endoscope to prevent its substantial movement.

The endoscope locking assembly desirably addresses the problem related to unwanted movement of the endoscope while the instrument is advanced into tissue for penetration or dissection. This assembly is adapted to constrict the shaft lumen and engage the endoscope when it is inserted through the shaft. It prevents substantial movement of the shaft when the endoscope locking assembly is engaged. It prevents such movement both radially and axially, therefore maintaining the endoscope in a fixed position during the advancement of the instrument. The fixed endoscope is important to the surgeon's ability to perform the penetration or dissection without any significant disruption resulting from an unwanted change in the orientation of the visual image created by the endoscope. Therefore, optimum clarity and visual imaging can be readily obtained, without any unwanted distractions.

The surgical instrument of this invention is ideally suited for all applications for which conventional trocars and other instruments for creating space are used. These applications include, but are not limited to, various forms of endoscopic surgery, including laparoscopic and thoracoscopic surgery. It is also envisioned that the surgical instrument of this invention may be used for arthroscopic surgery as well. In addition to those procedures where penetration and puncture of the body wall to provide a passageway for additional endoscopic surgical instrumentation is desired, it is also anticipated that this instrument may be used in procedures not requiring complete penetration and puncture through the body wall. For example, certain procedures require a penetrating or dissecting instrument to tunnel through layers of tissue without breaking certain other layers of tissue. Emerging procedures in connection with laparoscopic hernia repair and saphenous vein harvesting for cardiovascular surgery incorporate tunneling techniques to provide access to a desired surgical site remote from the point of entry. The surgical user may well find the surgical instrument of this invention, which offers the dual capabilities of dissection and visualization, to be particularly well suited for these emerging procedures. Finally, the reader must also realize that although this instrument is particularly adapted for endoscopic surgical applications, it may also find use for a wealth of applications in conventional open surgery.

BRIEF DESCRIPTION OF THE DRAWINGS

FIG. 1 is a perspective view of an assembly including the surgical penetration instrument of the present invention.

FIG. 2 is an enlarged perspective view of the penetrating tip of the instrument, and the relationship between the distal end of an endoscope and the proximal end of the penetrating tip.

FIG. 3 is a side elevational view in partial cross-section of the assembly including the instrument shown in the process of penetrating bodily tissue in a surgical patient.

DETAILED DESCRIPTION OF THE PREFERRED EMBODIMENT

Figure 4:
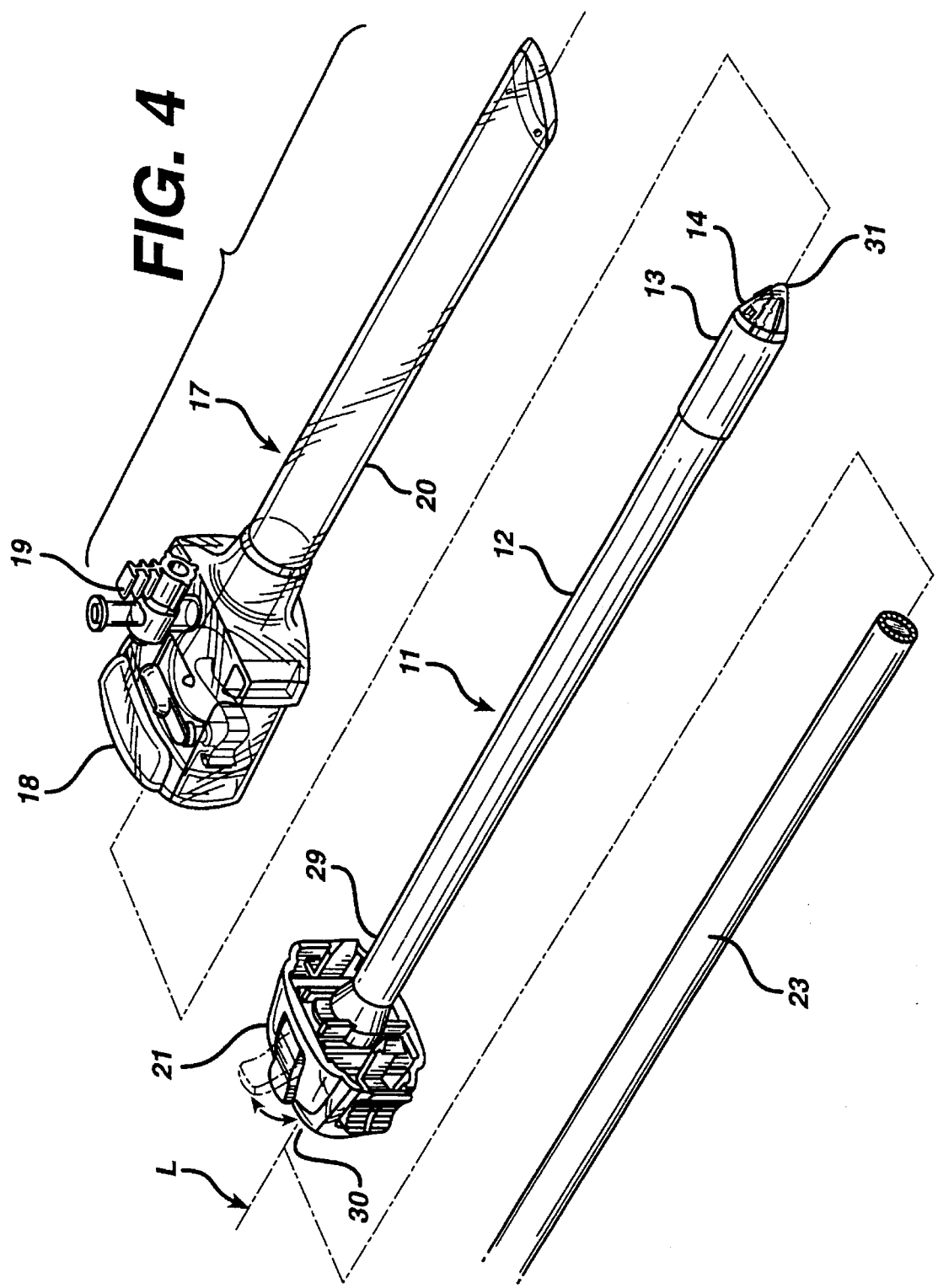
FIG. 4 is an exploded perspective view of the assembly including the surgical penetration instrument.

Reference numerals are used in this description to designate the various components and elements of the surgical instrument of this invention. Identical reference numerals designated in the various drawings refer to the identical element or component of the surgical penetration instrument. As used in this description, "proximal" or "proximally" refers to that portion of the instrument, component or element which extends toward the user. Conversely, "distal" or "distally" refers to that portion of the instrument, component or element which extends away from the user.

Referring now to FIGS. 1,2 and 4, there is shown an assembly 10 which incorporates the surgical penetration or dissection instrument of this invention. The surgical instrument 11 has a cylindrical, elongated hollow shaft 12. The shaft has a proximal end 29 and distal end 13 from which extends a conical transparent penetrating tip 14. The shaft also has a longitudinal axis designated by the letter "L" in FIG. 4. Facilitating the penetration of tip 14 as instrument 11 is advanced into tissue in the direction of the shaft longitudinal axis are first and second blades 15 and 16, respectively, extending outwardly from the transparent conical tip.

The assembly includes a conventional cannula 17. The cannula has a cannula housing 18 and stopcock 19. Extending distally from the cannula housing 18 is the cannula sleeve 20. The surgical instrument 11 is inserted into and through the cannula housing 18 and sleeve 20. The transparent penetrating tip 14 of the instrument, and a portion of the shaft distal end 13 of the instrument, extend distally from the cannula sleeve 20.

A hub 21 is attached to the shaft proximal end 29 of the surgical instrument. The hub can be secured to the cannula housing 18 using a conventional attachment mechanism when the shaft is fully inserted into and through the cannula housing and sleeve. The hub has a passageway 30 communicating with the lumen of the hollow shaft 12. If desired, a pressurizing fluid such as carbon dioxide can be selectively pumped through the cannula sleeve 20 via stopcock 19 into the body of the patient.

The assembly illustrated in FIG. 1, and in particular the surgical penetration or dissection instrument 11 of this invention, can be used to penetrate or dissect tissue while providing simultaneous visualization as the tissue is penetrated or dissected. As illustrated in FIG. 3, the assembly 10 is advanced in the direction illustrated by the arrow through bodily tissue 24 of a surgical patient 25. A conventional endoscope 23 can be inserted through the passageway 30 of hub 21 and the hollow shaft 12 of instrument 11 so that the endoscope is positioned adjacent the proximal end of transparent penetrating tip 14. The endoscope 23 is connected to a light source 21 to provide illumination through the transparent penetrating tip 14 to the surgical site. It is also connected to a video monitor 22 to display the illuminated images transmitted from the surgical site. In this way, the user can readily monitor the advance of instrument 11 through bodily tissue 24 from video monitor 22.

When the advancement of the surgical instrument 11 is completed, the instrument and the endoscope 23 may be removed from cannula 17 of assembly 10, so that additional instrumentation can then be inserted through the cannula to the surgical site to complete a desired surgical procedure.

Referring now to FIGS. 2, the transparent, conical penetrating tip 14 of the surgical instrument has a circular base 26 and a blunt point 31 extending distally from the base. The circular base 26 is positioned adjacent the shaft distal end 13. The first and second blades 15 and 16, respectively, have generally straight, linear edge surfaces 27 and 28, respectively. Each of the first and second blades 15 and 16 extend longitudinally from adjacent the circular base 26 toward point 31 of penetrating tip 14. The first and second blades are spaced about 180° from each other, and are positioned proximally of the point.

Figure 5:
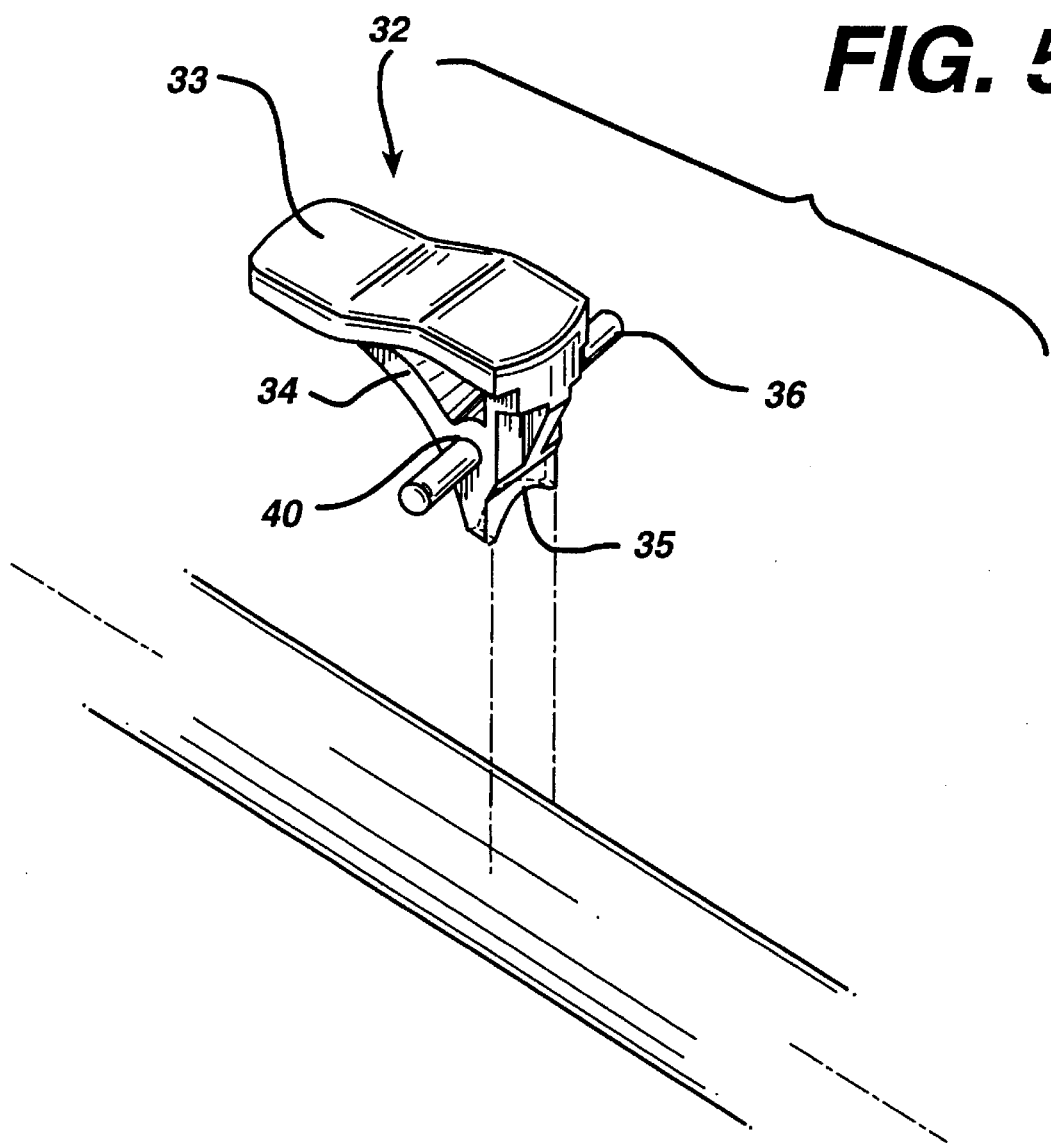
FIG. 5 is an exploded perspective view showing the locking assembly of the surgical instrument of this invention suspended above the shaft of an endoscope.
Figure 6:
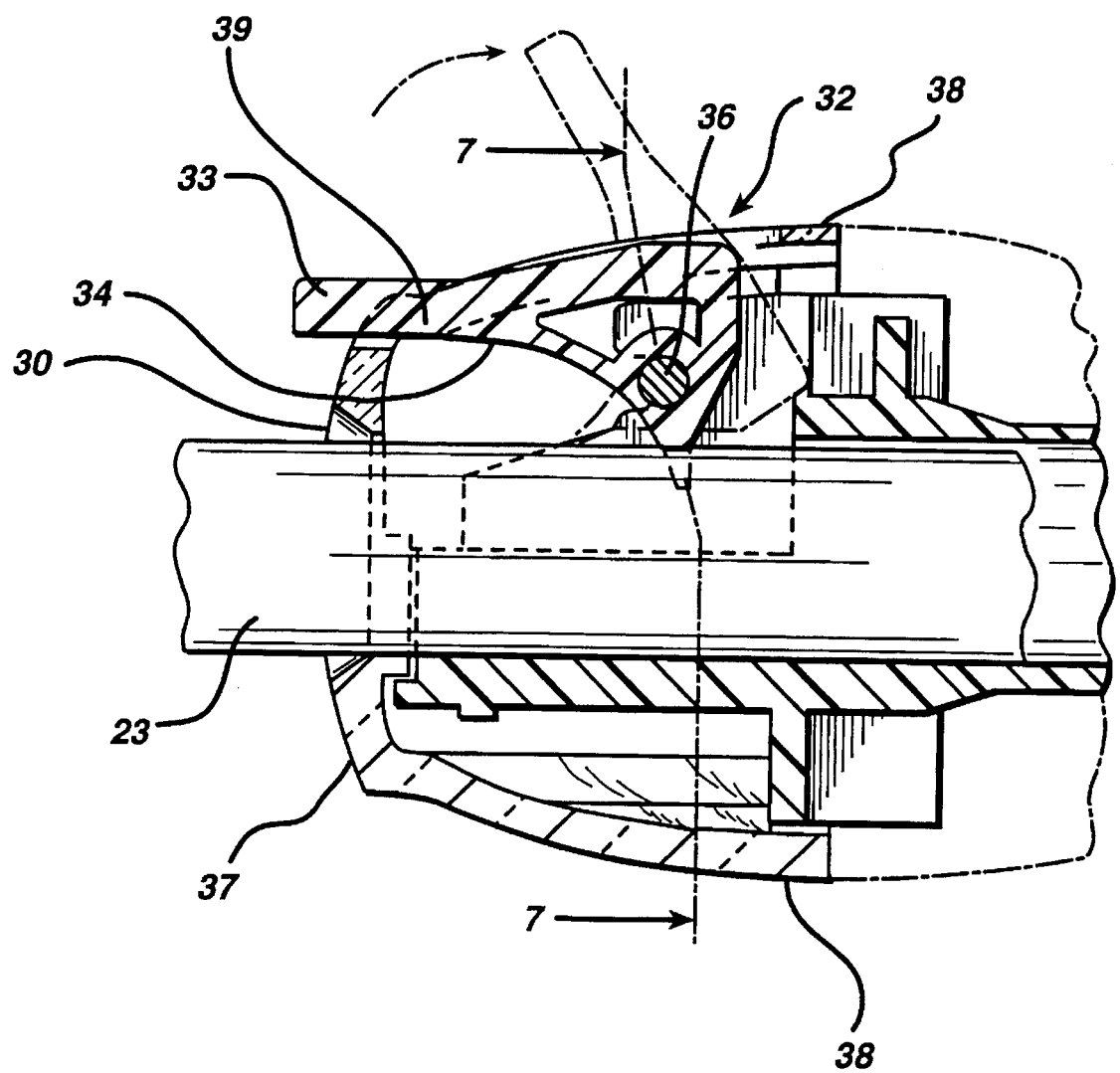
FIG. 6 is a partial longitudinal cross-sectional view of the locking assembly taken along section line 6—6 of FIG. 1.
Figure 7:
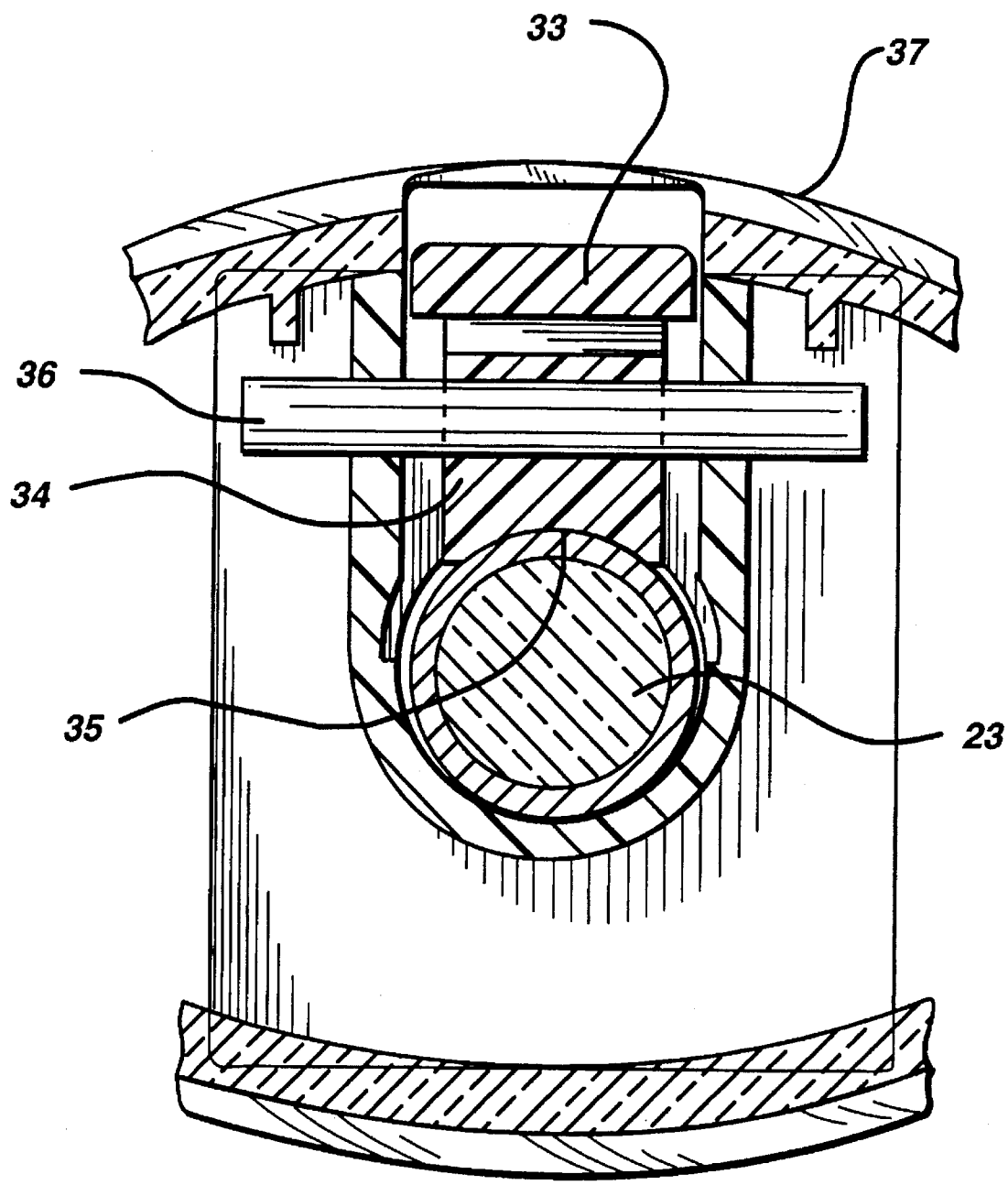
FIG. 7 is a transverse cross-sectional view of the locking assembly taken along line 7—7 of FIG. 6.

What will now be described is the locking assembly of the surgical instrument which restricts substantial movement of the endoscope 23 when the endoscope is received within the hollow shaft 12 and extends in abutting relationship with penetrating tip 14 at the shaft distal end 13. Referring to FIGS. 5-7, the locking assembly is designated generally at 32. The locking assembly includes a finger latch 33 which a user can readily engage to actuate the assembly 32 from an open to a closed position, and vice versa. Extending away from the underside of the proximal end of the finger latch 33 is a camming member 34. The camming member 34 has an arcuate configuration which terminates at an arcuate camming edge surface 35 spaced from the distal end of the finger latch 33. An aperture 40 extends laterally through camming member 34 adjacent the arcuate camming edge surface 35. Camming member 34 is mounted on a rod 36 through the aperture 40 for rotational movement of the locking assembly from an open to a closed position.

The rod 36 of the locking assembly 32 is fixed within the hub 21 using a conventional attachment method. The rod is positioned generally perpendicularly to the longitudinal axis of the elongated shaft 12 of the surgical instrument. The hub 21 has a top surface 37 from which extends distally two side surfaces, each of which is designated as 38. The rod 36 is therefore positioned proximally of top surface 37 and between the two side surfaces 38.

The hollow shaft 12 extends into the hub 21 to a position adjacent the top surface 37 of the hub. An opening in the shaft within the hub 21 is created to permit the free rotational movement of the locking assembly.

One of the side surfaces 38 contains a longitudinally extending slot 39. When the locking assembly is in the closed position, the finger latch 33 rests within and parallel to the longitudinally extending slot 39. In the closed position, the finger latch is congruous with side surface 38 of hub 21, and extends slightly proximally beyond the top surface 37. The user can therefore readily engage that portion of the finger latch 33 which extends proximally from top surface 37 when the user desires to actuate the locking assembly from the closed position to the open position.

When the user desires to actuate the locking assembly from a closed position to an open position, the user engages the finger latch 33 and moves it in the direction of the arrow illustrated in FIG. 6. Since the camming member extending arcuately away from the finger latch 33 is mounted for rotational movement on the axially stationary rod 36 within hub 31, upward movement of the finger latch 33 will cause the entire locking assembly to rotate about the fixed rod 36. In the open position the finger latch 33 protrudes laterally from the slot 39 and side surface 38. The angular relationship of the finger latch between the open and closed positions is about 60°, and further movement of the finger latch beyond the open position illustrated by the dashed lines of FIG. 6 is prevented because the finger latch contacts a portion of the inner structure within hub 21.

When the locking assembly is in the closed position, the arcuate camming surface 35 extends into the lumen of the hollow shaft 12 at the shaft proximal end 29 within hub 21. As best illustrated in FIG. 7, when the locking assembly is in the closed position, and the endoscope 23 is inserted through the passageway 30 and the hollow shaft 12 of the instrument, the arcuate camming edge surface 35 constricts the size of the shaft lumen to substantially restrict rotational or axial movement of endoscope 23. The arcuate camming edge surface 35 has a radius of curvature which corresponds to that of the endoscope 23, and so therefore when the locking assembly is in the closed position, the arcuate camming edge surface 35 frictionally engages the outer arcuate surface of the endoscope to prevent substantial movement.

When the locking assembly is returned to the open position by moving the finger latch 33 in the upward direction as shown in FIG. 6, the rotational movement of the camming member 34 causes the arcuate camming edge surface 35 to move into a position where it no longer constricts the size of the shaft lumen within hub 21. Therefore, the endoscope 23 can be freely inserted into and withdrawn from hollow shaft 12.

The reader should realize that this detailed description of the most preferred embodiment of the surgical instrument of this invention does not preclude numerous embodiments which are not particularly illustrated in the drawings from falling within the scope of the appended claims. In other words, it is the appended claims which define the scope of the invention, and not this detailed description. One skilled in the art can readily envision numerous additional embodiments which fall within the scope of the appended claims. For example, the claimed invention should in no way be construed to be limited to a surgical penetration instrument which has a transparent penetrating tip. A penetrating tip may be unnecessary or undesirable when the instrument is used to gently dissect soft tissue. Additionally, if a penetrating tip is desired, it may be desirable to modify its shape for different applications, and further, it may be desirable to modify the number or configuration of blades which may extend outwardly from the tip.

What is claimed is:

1. A surgical instrument for penetrating or dissecting bodily tissue, said instrument comprising a generally cylindrical, elongated hollow shaft having a longitudinal axis and proximal and distal ends, said hollow shaft having a lumen therethrough with a diameter sized to slidably receive an endoscope therein from said shaft proximal end to said shaft distal end; a hub attached to said shaft proximal end having a passageway therethrough communicating with said shaft lumen; and an endoscope locking assembly on said hub, said locking assembly including a camming member therein, said camming member terminating at an arcuate camming edge surface; wherein when said endoscope is received in said shaft lumen, said locking assembly is actuable from an open position wherein said arcuate camming edge surface of said camming member of said locking assembly is spaced from said shaft lumen and disengaged from said endoscope, to a closed position wherein said arcuate camming edge surface constricts said shaft lumen and engages said endoscope so as to prevent substantial movement thereof.

2. The instrument of claim 1 wherein said hub has a top surface adjacent said shaft proximal end, and a side surface extending distally from said top surface and spaced apart from said shaft proximal end, said side surface having a longitudinally extending slot therein.

3. The instrument of claim 2 wherein said locking assembly includes an engagable finger latch for actuating said locking assembly from said open to said closed positions, said latch disposed in said slot.

4. The instrument of claim 3 wherein said latch extends outwardly of said side surface in said open position and lies generally parallel to and substantially in alignment with said side surface in said closed position.

5. The instrument of claim 4 wherein said camming member of said locking assembly diverges from said latch within said hub, and said arcuate camming edge surface of said camming member has a radius of curvature substantially the same as that of said shaft lumen.

6. The instrument of claim 5 wherein said locking assembly includes an axially stationary rod disposed within said hub and substantially perpendicular to said shaft longitudinal axis, and said camming member is rotatably mounted on said rod, wherein when said camming member is rotated from said open to said closed position using said latch, said arcuate camming edge surface rotates from a first position spaced from said shaft lumen for slidably receiving said endoscope therein, to a second camming position constricting said shaft lumen for fictionally resisting substantial movement of said endoscope.

7. The instrument of claim 6 wherein said instrument further comprises a penetrating tip extending from said shaft distal end and having a transparent portion, said tip having an exterior surface configuration shaped to enlarge an opening as said instrument is advanced into said bodily tissue.

\* \* \* \* \*